United States Patent [19]
Crum et al.

[11] Patent Number: 5,954,861
[45] Date of Patent: Sep. 21, 1999

[54] PROCESS FOR RECOVERY OF METHYL CHLORIDE

[75] Inventors: Bruce Robert Crum, Madison, Ind.; Corey Grant Knutson, Burlington, Ky.; Brian Michael Naasz, DeWitt, Mich.; Jeffrey Scott Smith, Baton Rouge, La.

[73] Assignee: Dow Corning Corporation, Midland, Mich.

[21] Appl. No.: 08/293,611

[22] Filed: Aug. 19, 1994

[51] Int. Cl.⁶ ..................................... B01D 53/14
[52] U.S. Cl. ................ 95/166; 95/168; 95/169; 95/182; 95/191; 95/207; 95/211; 95/237
[58] Field of Search .............................. 95/162, 168, 171, 95/182, 187, 191, 207, 211, 233, 237–240, 166, 169

[56] References Cited

U.S. PATENT DOCUMENTS

| | | | |
|---|---|---|---|
| 3,148,041 | 9/1964 | Dehn et al. .................................. | 55/31 |
| 3,883,642 | 5/1975 | Franke et al. ......................... | 95/233 X |
| 4,020,117 | 4/1977 | Sisson ..................................... | 260/652 |
| 4,039,597 | 8/1977 | Taso ........................................ | 260/659 |
| 4,102,983 | 7/1978 | Yamase et al. ....................... | 95/211 X |
| 4,193,944 | 3/1980 | Tsao et al. ........................... | 260/659 R |
| 4,923,485 | 5/1990 | Höroldt et al. ....................... | 95/239 X |
| 5,071,454 | 12/1991 | Streitberger et al. ..................... | 95/237 |

*Primary Examiner*—Robert Spitzer
*Attorney, Agent, or Firm*—William F. Boley

[57] ABSTRACT

A process for separating a gaseous mixture comprising $C_1$ chlocarbons and noncondensible gases into a liquid component comprising the $C_1$ chlorocarbons and a component comprising the noncondensible gases. The method employs a liquid hydrocarbon having an average molecular weight within a range of about 142 to 422 to adsorb the $C_1$ chlorocarbons from the gaseous mixture. The present process is especially useful for separating methyl chloride from a gaseous mixture resulting from an oxychlorination process where the gaseous mixture further comprises, methane, water vapor, and hydrogen chloride.

18 Claims, No Drawings

PROCESS FOR RECOVERY OF METHYL CHLORIDE

BACKGROUND OF INVENTION

The present invention is a process for separating a gaseous mixture comprising $C_1$ chlorocarbons and noncondensible gases into a liquid component comprising the $C_1$ chlorocarbons and a component comprising the noncondensible gases. The method employs a liquid hydrocarbon having an average molecular weight within a range of about 142 to 422 to adsorb the $C_1$ chlorocarbons from the gaseous mixture. The present process is especially useful for separating methyl chloride from a gaseous mixture resulting from an oxychlorination process where the gaseous mixture further comprises, methane, water vapor, and hydrogen chloride.

It is known to chlorinate methane by a process typically termed "oxychlorination." In processes of this type, gaseous hydrogen chloride and an oxygen containing gas such as air and the hydrocarbon to be chlorinated are contacted with a metal halide catalyst which may also comprise stabilizers and promoters. By a series of well known reactions, elemental chlorine ($Cl_2$) is released from the hydrogen chloride and chlorinates the hydrocarbon feed material. In another modification of this process, elemental chlorine ($Cl_2$) is used as the feed gas in place of gaseous HCl. This latter process operates in a manner similar to the first except that an initial chlorination of hydrocarbon takes place. Thus, free chlorine, and oxygen containing gas, and the hydrocarbon to be chlorinated are contacted with the metal halide catalyst. The chlorine reacts with the hydrocarbon to produce hydrogen chloride and a chlorinated product of the hydrocarbon. Hydrogen chloride produced in this manner is then converted to elemental chlorine by a well known series of reactions, thereby providing additional chlorine for the chlorination of more hydrocarbon feed.

Although oxychlorination processes of this type are well known in the art, there are serious operational difficulties generally associated with them. For example, it is found that serious difficulty arises in the recovery of the chlorinated hydrocarbon products produced by such reactions. This is due in part to the fact that the chlorinated hydrocarbon products are diluted in great quantities of inert or noncondensible gases such as methane, elemental nitrogen, carbon monoxide, carbon dioxide, and other like gases. In order to recover the products satisfactorily from such a process it is necessary to process large quantities of gas and efficiently recover the chlorinated hydrocarbon content thereof.

The recovery process is further complicated by the presence of water and hydrogen chloride in such mixtures which can condense to form an aqueous hydrogen chloride solution. This aqueous hydrogen chloride solution can not only be detrimental to process equipment but may also have deleterious effects on solvents used in separation processes.

Deim et al., U.S. Pat. No. 3,148,041, describe a process where a gaseous mixture containing chlorinated methanes and predominating quantities of noncondensible gaseous components is contacted with a liquid aromatic halogenated hydrocarbon after scrubbing with an aqueous alkaline solution to remove hydrogen chloride. Deim et al. report that with this process it is possible to absorb essentially all of the chlorinated methane content of such a mixture while permitting the non-chlorinated methane and noncondensible gases to pass through the absorbent.

Taso, U.S. Pat. No. 4,039,597, teaches that chlorinated hydrocarbons may be separated from a gas stream containing unreacted hydrocarbon, carbon dioxide, and chlorinated hydrocarbons by such processes as condensation and fractionation.

Sisson, U.S. Pat. No. 4,020,117, describes a process for recovering methyl chloride and methylene chloride from the effluent of an oxychlorination process. The process comprises cooling the effluent and contacting with an absorbent that is specific for the methyl chloride and dichloromethane. The absorbent is then stripped with methane to recover the methyl chloride and dichloromethane.

Taso et al., U.S. Pat. No. 4,193,944, describe a process where a purge stream containing inerts, unreacted alkane and chlorinated hydrocarbon is recovered from a chlorinated hydrocarbon production effluent. The purge gas is contacted with an absorption oil recovered from the effluent which is at least one chlorinated hydrocarbon boiling at a temperature of at least 140° C. to absorb chlorinated hydrocarbon.

The present process offers advantages over the described prior art processes for recovering $C_1$ chlorocarbons from a gaseous mixture with noncondensible gases. The present process employs a liquid hydrocarbon having an average molecular weight within a range of about 142 to 422 to adsorb the $C_1$ chlorocarbons from the gaseous mixture. The described liquid hydrocarbon is stable at elevated temperatures in the presence of aqueous hydrogen chloride. Therefore it is not necessary to treat the gaseous mixture to neutralize, as taught by Diem et al., supra, when the adsorption media is a halogenated aromatic hydrocarbon. The described process allows large volumes of gases containing less than about 25 percent $C_1$ chlorocarbons to be processed more economically to recover the $C_1$ chlorocarbons than can be achieved by methods such as condensation and fractionation as suggested by Taso, supra. In addition, the adsorbed $C_1$ chlorocarbons can be stripped from the described liquid hydrocarbon with very little carryover, allowing the liquid hydrocarbon to be continuously recycled to the process. Furthermore, use of the liquid hydrocarbon avoids environmental issues associated with the use of halogenated hydrocarbons.

SUMMARY OF INVENTION

The present invention is a process for separating a gaseous mixture comprising $C_1$ chlorocarbons and noncondensible gases into a liquid component comprising the $C_1$ chlorocarbons and a component comprising the noncondensible gases. The method employs a liquid hydrocarbon having an average molecular weight within a range of about 142 to 422 to adsorb the $C_1$ chlorocarbons from the gaseous mixture. The present process is especially useful for separating methyl chloride from a gaseous mixture resulting from an oxychlorination process where the gaseous mixture further comprises, methane, water vapor, and hydrogen chloride.

DESCRIPTION OF INVENTION

The present invention is a process for recovering a $C_1$ chlorocarbon from a gaseous mixture. The process comprises: contacting a gaseous mixture comprising a $C_1$ chlorocarbon and one or more noncondensible gases with an absorbent comprising a liquid hydrocarbon having an average molecular weight within a range of about 142 to 422 at a temperature and pressure where the $C_1$ chlorocarbon is absorbed by the liquid hydrocarbon thereby separating the $C_1$ chlorocarbon from the noncondensible gas.

The present process is useful for separating $C_1$ chlorocarbons from gaseous mixtures comprising one or more $C_1$ chlorocarbons and noncondensible gases. The present process is especially useful for recovering $C_1$ chlorocarbons from oxychlorination processes for forming methyl chloride. Such oxychlorination processes are well known to those skilled in the art and need not be described in detail herein. A typical oxychlorination process consists of feeding methane or natural gas, an oxygen source, and a chlorine source such as hydrogen chloride or chlorine gas to a reactor containing a copper halide melt and appropriate stabilizing and activating compounds. The effluent from this process typically consists of methyl chloride; lessor amount of more chlorinated $C_1$ chlorocarbons such as dichloromethane and chlorinated $C_2$ or higher components; unreacted methane and oxygen; oxidation products such as carbon dioxide and carbon monoxide; hydrogen chloride; and minor amounts of water.

$C_1$ chlorocarbons which can be recovered by the present process can include methyl chloride, dichloromethane, trichloromethane, and tetrachloromethane. The preferred $C_1$ chlorocarbon is methyl chloride.

The gaseous mixture from which the $C_1$ chlorocarbon is recovered comprises one or more noncondensible gases. By "noncondensible" it is meant that the gas is not significantly condensed under the process temperature and pressure conditions as described herein. The present process is especially useful for separating $C_1$ chlorocarbons from a gaseous mixture comprising such noncondensible gases as methane, oxygen, carbon dioxide, nitrogen, and the like. A preferred gaseous mixture for use in the present process is one which comprises, in addition to methyl chloride; methane, hydrogen chloride, and water vapor.

The gaseous mixture is contacted with an absorbent comprising a liquid hydrocarbon having an average molecular weight within a range of about 142 to 422. The liquid hydrocarbon is nonhalogenated. Preferred is a substantially-branched liquid hydrocarbon having an average molecular weight within a range of about 142 to 422. More preferred is a substantially-branched liquid hydrocarbon having an average molecular weight of about 272. Most preferred is when the liquid hydrocarbon is a substantially-branched hydrogenated dimer of 1-decene having an average molecular weight of about 272. By "substantially-branched" it is meant that the liquid hydrocarbon has a major component with variable amounts of short branches relative to the backbone carbon-carbon chain.

Contact of the gaseous mixture with the liquid hydrocarbon can be by standard methods for effecting the contact of gases and liquids. The contact can be effected for example in packed, unpacked, bubble cap, perforated plate, and other similar type columns used to effect the contact of a gas with a liquid. Preferred is when the contact of the gaseous mixture with the liquid hydrocarbon is effected in a packed column. The column can be packed with for example, glass or teflon beryl saddles or Raschig rings. The gaseous mixture and liquid hydrocarbon can be fed to the column as cocurrent feeds or as countercurrent feeds. Preferred is when the gaseous mixture and liquid hydrocarbon are fed to a packed column in a countercurrent manner.

The mass ratio of liquid hydrocarbon to gaseous mixture (L/G) contacted in the present process can be varied within wide limits. The lower limit for the L/G ratio is dependent upon the efficiency of removal of the $C_1$ chlorocarbon from the gaseous mixture. In general, under the present process conditions a L/G ratio of about four is considered to be a lower limit. The upper limit for the L/G ratio is limited by the acceptable levels of dilution of the $C_1$ chlorocarbon in the liquid hydrocarbon and the maximum liquid loading of the column used. Generally under the process conditions defined herein, it is preferred that the L/G ratio be within a range of about 10:1 to 30:1.

The temperature at which the contact of the gaseous mixture with the liquid hydrocarbon is effected can generally be any temperature at which the $C_1$ chlorocarbon is absorbed by the liquid hydrocarbon and the noncondensible gas from which separation is desired is not condensed. Generally, the lower the temperature the more effective the recovery of the $C_1$ chlorocarbon from the gaseous mixture. A temperature within a range of about $-58°$ C. to $40°$ C. is considered useful, with the minimum useful temperature being the freezing point of the acid and water mixture present. More preferred is a temperature within a range of about $-30°$ C. to $10°$ C., with a temperature within a range of about $-20°$ C. to $0°$ C. being most preferred. In a preferred process where the gaseous mixture comprises, in addition to the $C_1$ chlorocarbons and noncondensible gases, hydrogen chloride and water, a preferred temperature is one where aqueous hydrogen chloride is condensed in mixture with the liquid hydrocarbon containing the $C_1$ chlorocarbons.

In the present process contact of the gaseous mixture with the liquid hydrocarbon can be effected at a pressure within a range of about 0 psig (0 kPa) to 175 psig (1206 kPa). More preferred is a pressure within a range of about 15 psig (103 kPa) to 100 psig (689 kPa). Most preferred is a pressure within a range of about 20 psig (138 kPa) to 50 psig (345 kPa).

A noncondensible gas and a liquid mixture comprising the liquid hydrocarbon containing the $C_1$ chlorocarbon is recovered from the present process. By "recovered" it is meant that the noncondensible gas and liquid hydrocarbon containing the $C_1$ chlorocarbon are removed from the contact area. The recovered noncondensible gas may be, for example, incinerated to recover caloric value or further separated to recover useful materials or to facilitate appropriate disposal.

The recovered liquid mixture comprising the liquid hydrocarbon containing the $C_1$ chlorocarbon can be further separated by standard methods to recover the $C_1$ chlorocarbon and the liquid hydrocarbon can then be recycled to the process. The $C_1$ chlorocarbon can be separated from the liquid hydrocarbon by, for example, a stripping process where the recovered liquid mixture is heated to a temperature and pressure causing vaporization of the $C_1$ chlorocarbon and substantially no vaporization of the liquid hydrocarbon. In a preferred method, the $C_1$ chlorocarbon is separated from the liquid hydrocarbon by steam stripping at a temperature within a range of about $45°$ C. to $185°$ C. at about 20 psig (138 kPa) to 50 psig (345 kPa) pressure. More preferred is when the stripping is accomplished at a temperature within a range of about $90°$ C. to $115°$ C. at a pressure within a range of about 35 psig (241 kPa) to 45 psig (310 kPa). Stripping columns employed may be packed, unpacked, bubble cap, perforated plate, and the like. Preferred, is a packed column using beryl saddles or Raschig rings.

The liquid mixture comprising the liquid hydrocarbon and the $C_1$ chlorocarbon may also contain other components such as aqueous hydrogen chloride. Aqueous hydrogen chloride is not miscible with the liquid hydrocarbon containing the $C_1$ chlorocarbon and may be separated from the liquid hydrocarbon by standard methods for separating nonmiscible liquids. For example, the aqueous hydrocarbon may be separated in a phase separator apparatus by gravity settling. The recovered aqueous hydrogen chloride can be used as feed to another process such as an oxychlorination process. The liquid mixture comprising the liquid hydrocarbon and the $C_1$ chlorocarbon can then be stripped to recover the $C_1$ chlorocarbon as described above.

The following examples are provided to illustrate the present invention. These examples are not intended to limit the scope of the present claims.

EXAMPLE 1

The ability of a liquid hydrocarbon having an average molecular weight of 272 to separate methyl chloride from a mixture comprising the methyl chloride and a noncondensible gas was evaluated at various liquid/gas feed ratios and process pressures.

The separation process was conducted in a teflon column having an inside diameter of 1.6 cm. The column was packed to a height of 61 cm with 3.2 mm glass Raschig rings. During conduct of the separation process the exterior column wall was maintained at a temperature of about 0° C. Methyl chloride gas was mixed with nitrogen at the mole percents described in Table 1. The resulting gaseous mixtures were fed to the bottom of the column at a rate of 165 ml/min. (based on standard temperature and pressure volumes).

A liquid hydrocarbon having an average molecular weight of about 272 was fed to the top of the column at a rate sufficient to maintain the liquid to gas ratios (L/G) described in Table 1. The liquid hydrocarbon was a product of Multitherm Corporation, Colwyn, Pa., designated as Multitherm® 503. Multitherm 503 is described as a hydrogenated 1-decene dimer having an average molecular weight of 272, density at 16° C. of 0.798 g/cc, atmospheric boiling point of 329° C.

Nitrogen gas was collected from the top of the column. The liquid hydrocarbon was collected from the bottom of the column and analyzed by gas chromatography (GC) using a thermal conductivity detector (TC). The results are reported in Table 1 as the weight percent of methyl chloride in the feed mixture recovered in the liquid hydrocarbon.

TABLE 1

Methyl Chloride Recovery as Function of Selected Process Parameters

| Mole % MeCl | L/G | Press. (psig) | Wt. % MeCl Recovered |
|---|---|---|---|
| 10 | 20 | 30 (207 kPa) | 80.6 |
| 15 | 20 | 30 | 83.9 |
| 20 | 20 | 30 | 87.9 |
| 25 | 20 | 30 | 93.1 |
| 30 | 20 | 30 | 98.5 |
| 10 | 20 | 40 (276 kPa) | 93.0 |
| 15 | 20 | 40 | 93.8 |
| 20 | 20 | 40 | 94.9 |
| 25 | 20 | 40 | 96.6 |
| 30 | 20 | 40 | 96.7 |
| 10 | 30 | 30 (207 kPa) | 98.9 |
| 15 | 30 | 30 | 99.3 |
| 20 | 30 | 30 | 99.5 |
| 25 | 30 | 30 | 99.6 |
| 30 | 30 | 30 | 99.8 |
| 35 | 30 | 30 | 99.9 |
| 40 | 30 | 30 | 99.9 |

EXAMPLE 2

The ability of a liquid hydrocarbon having an average molecular weight of 272 to separate methyl chloride from a gaseous mixture resulting from an oxychlorination process was evaluated.

The separation process was conducted in a packed column similar to that described in Example 1. The outer wall temperature of the column was kept at about 0° C. A gaseous mixture resulting from an oxychlorination process, where methane, oxygen, hydrogen chloride, and nitrogen were fed to the process, was fed to the bottom of the packed column. The gaseous mixture contained about 7 mole percent methyl chloride, 41 mole percent methane, 40 mole percent nitrogen, and minor amounts of carbon dioxide. The liquid hydrocarbon was fed to the top of the column at a rate sufficient to provide the liquid/gas ratios described in Table 2 under the Heading "L/G". The pressure of the column was maintained at about 30 psig (207 kPa) throughout the process. The liquid hydrocarbon was Multitherm 503, as previously described. Non-condensible gases were collected from the top of the column and a liquid fraction comprising the liquid hydrocarbon containing methyl chloride and aqueous hydrogen chloride was collected from the bottom of the column over a several hour time period. The liquid hydrocarbon containing methyl chloride was separated from the aqueous hydrogen chloride by phase separation and analyzed by GC-TC for methyl chloride content at various time intervals. The average weight percent of methyl chloride (Wt. % MeCl Recovered) in the feed mixture recovered in the liquid hydrocarbon is reported in Table 2 along with the standard deviation and the number of samplings.

TABLE 2

Methyl Chloride Recovery From Gaseous Mixture Resulting from Oxychlorination Process

| L/G | Ave. Mole % MeCl Recovered |
|---|---|
| 20.0 | 73 ± 1 (n = 4) |
| 30.0 | 100 ± 0 (n = 3) |
| 13.5 | 24 ± 7 (n = 5) |

We claim:

1. A process for recovering a $C_1$ chlorocarbon from a gaseous mixture, the process comprising: contacting a gaseous mixture comprising a $C_1$ chlorocarbon and a noncondensible gas with an absorbent comprising a liquid hydrocarbon having an average molecular weight within a range of about 142 to 422 at a temperature and pressure where the $C_1$ chlorocarbon is absorbed in the liquid hydrocarbon thereby separating the $C_1$ chlorocarbon from the noncondensible gas.

2. A process according to claim 1, where the $C_1$ chlorocarbon is methyl chloride.

3. A process according to claim 1, where the gaseous mixture comprises methyl chloride, methane, hydrogen chloride, and water vapor.

4. A process according to claim 1, where the absorbent comprises a substantially-branched liquid hydrocarbon having an average molecular weight within a range of about 142 to 422.

5. A process according to claim 1, where the absorbent comprises a substantially-branched liquid hydrocarbon having an average molecular weight of about 272.

6. A process according to claim 1, where the absorbent comprises a substantially-branched hydrogenated dimer of 1-decene having an average molecular weight of about 272.

7. A process according to claim 1, where the mass ratio of absorbent to gaseous mixture is within a range of about 4:1 to 30:1.

8. A process according to claim 1, where the temperature is within a range of about −58° C. to 40° C.

9. A process according to claim 1, where the temperature is within a range of about −30° C. to 10° C.

10. A process according to claim 1, where the temperature is within a range of about −20° C. to 0° C.

11. A process according to claim 1, where the pressure is within a range of about 0 psig (0 kPa) to 175 psig (1206 kPa).

12. A process according to claim 1, where the pressure is within a range of about 15 psig (103 kPa) to 100 psig (689 kPa).

13. A process according to claim 1, where the pressure is within a range of about 20 psig (138 kPa) to 50 psig (345 kPa).

14. A process according to claim 1, where the $C_1$ chlorocarbon is recovered from the absorbent by steam stripping.

15. A process according to claim 14, where the steam stripping is accomplished at a temperature within a range of about 45° C. to 185° C. and a pressure of about 20 psig (138 kPa) to 50 psig (345 kPa).

16. A process according to claim 14, where the steam stripping is accomplished at a temperature within a range of about 90° C. to 115° C. and a pressure within a range of about 35 psig (241 kPa) to 45 psig (310 kPa).

17. A process for separating methyl chloride from a gaseous mixture, the process comprising:

(A) contacting in a packed-bed column a gaseous mixture comprising methyl chloride, hydrogen chloride, water, and one or more noncondensible gases selected from a group consisting of methane, oxygen, nitrogen, carbon monoxide, and carbon dioxide, with an absorbent comprising a substantially-branched liquid hydrocarbon having an average molecular weight of about 272, at a temperature within a range of about −20° C. to 0° C. and a pressure within a range of about 20 psig (138 kPa) to 50 psig (345 kPa) where the methyl chloride is absorbed in the liquid hydrocarbon and aqueous hydrogen chloride is formed, (B) recovering from the column the noncondensible gas and a liquid mixture comprising the liquid hydrocarbon containing the methyl chloride and the aqueous hydrogen chloride;

(C) separating the liquid mixture into a liquid hydrocarbon component containing the methyl chloride and an aqueous hydrogen chloride component, and (D) separating the methyl chloride from the liquid hydrocarbon component.

18. A process according to claim 17, where the methyl chloride is recovered from the liquid hydrocarbon by steam stripping and the liquid hydrocarbon is recycled to the process.

* * * * *